United States Patent [19]

Cody et al.

[11] Patent Number: 5,027,827
[45] Date of Patent: Jul. 2, 1991

[54] VACUUM BIOPSY APPARATUS

[76] Inventors: Michael P. Cody, 32 Magnolia St., Farmingham, Mass. 01701; Ashley Davidoff, 3, Lake Ave., Newton Centre, Mass. 02159; John R. Haaga, 3409 N. Hilltop, Chagrin Falls, Ohio 44022

[21] Appl. No.: 500,581

[22] Filed: Mar. 28, 1990

[51] Int. Cl.$^5$ .............................................. A61B 10/00
[52] U.S. Cl. .................................... 128/753; 128/764
[58] Field of Search ............... 128/749, 752, 753, 758, 128/764, 770

[56] References Cited

U.S. PATENT DOCUMENTS

| | | | |
|---|---|---|---|
| 2,822,808 | 2/1958 | Boone | 128/749 |
| 3,494,352 | 2/1970 | Russo et al. | 128/764 |
| 3,817,240 | 6/1974 | Ayres | 128/764 |
| 4,366,822 | 1/1983 | Altshuler | 128/753 |
| 4,549,554 | 10/1985 | Markham | 128/753 |
| 4,967,762 | 11/1990 | DeVries | 128/753 |

FOREIGN PATENT DOCUMENTS

| | | | |
|---|---|---|---|
| 0016633 | 10/1980 | European Pat. Off. | 128/764 |
| 0166574 | 1/1986 | European Pat. Off. | 128/764 |

OTHER PUBLICATIONS

Bruno D. Fornage, M.D., Fine-Needle Aspiration Biopsy with a Vacuum Test Tube Radiology, Nov. 1988:169:553:554.

Primary Examiner—Max Hindenburg
Attorney, Agent, or Firm—McAulay Fisher Nissen Goldberg & Kiel

[57] ABSTRACT

The vacuum biopsy apparatus includes a syringe having a side wall defining a chamber. It further includes a vacuum tube receivable within the syringe chamber. The vacuum tube has a septum at one end. The septum is shaped and dimensioned received within the syringe chamber with a fluid type fit. The vacuum tube and the septum are capable of movement within the syringe chamber to enable the vacuum tube to serve as the syringe plunger. Venting means are provided on the syringe side wall to prevent expelling air from the syringe when the vacuum tube is moved within the syringe chamber. The syringe includes mating means to allow the syringe to be connected to a biopsy needle. This allows communication between the biopsy needle and the vacuum tube when the vacuum tube is within the syringe chamber and the biopsy needle is connected to the syringe.

14 Claims, 4 Drawing Sheets

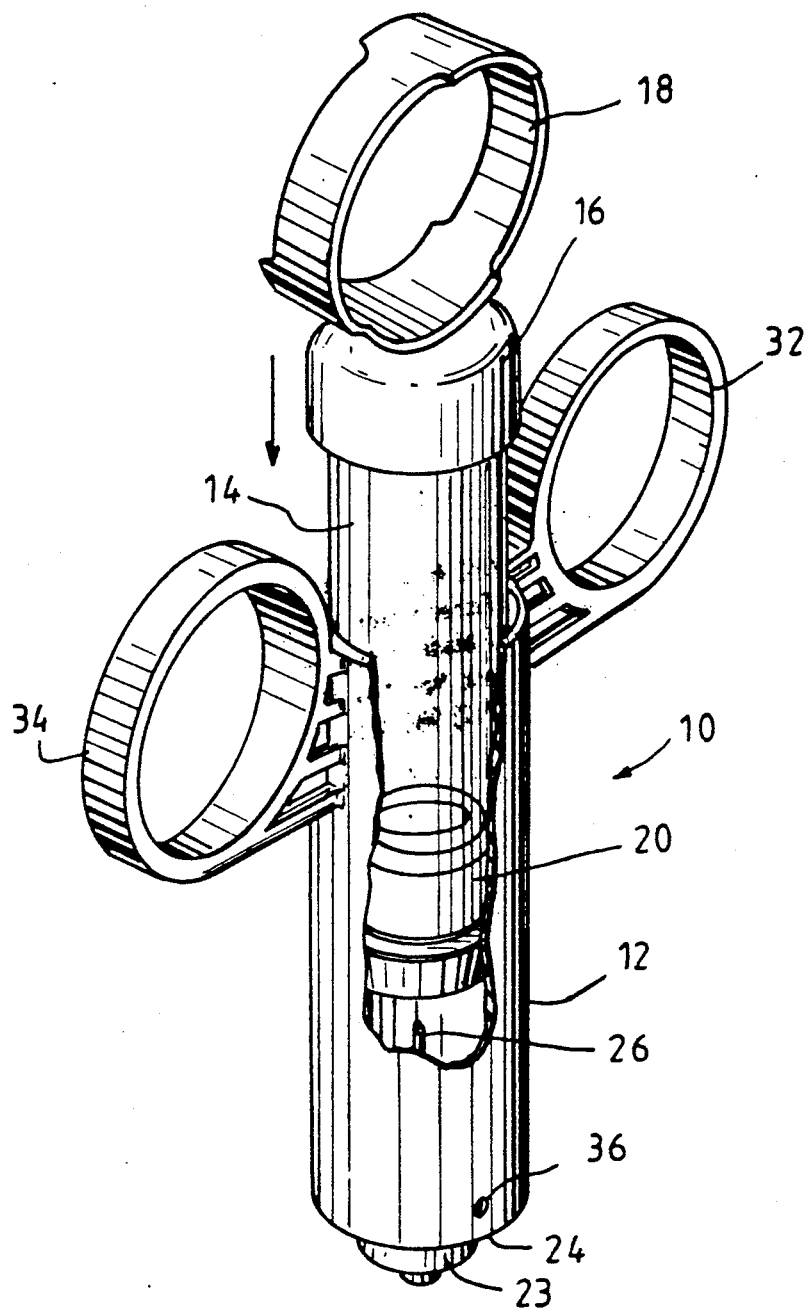

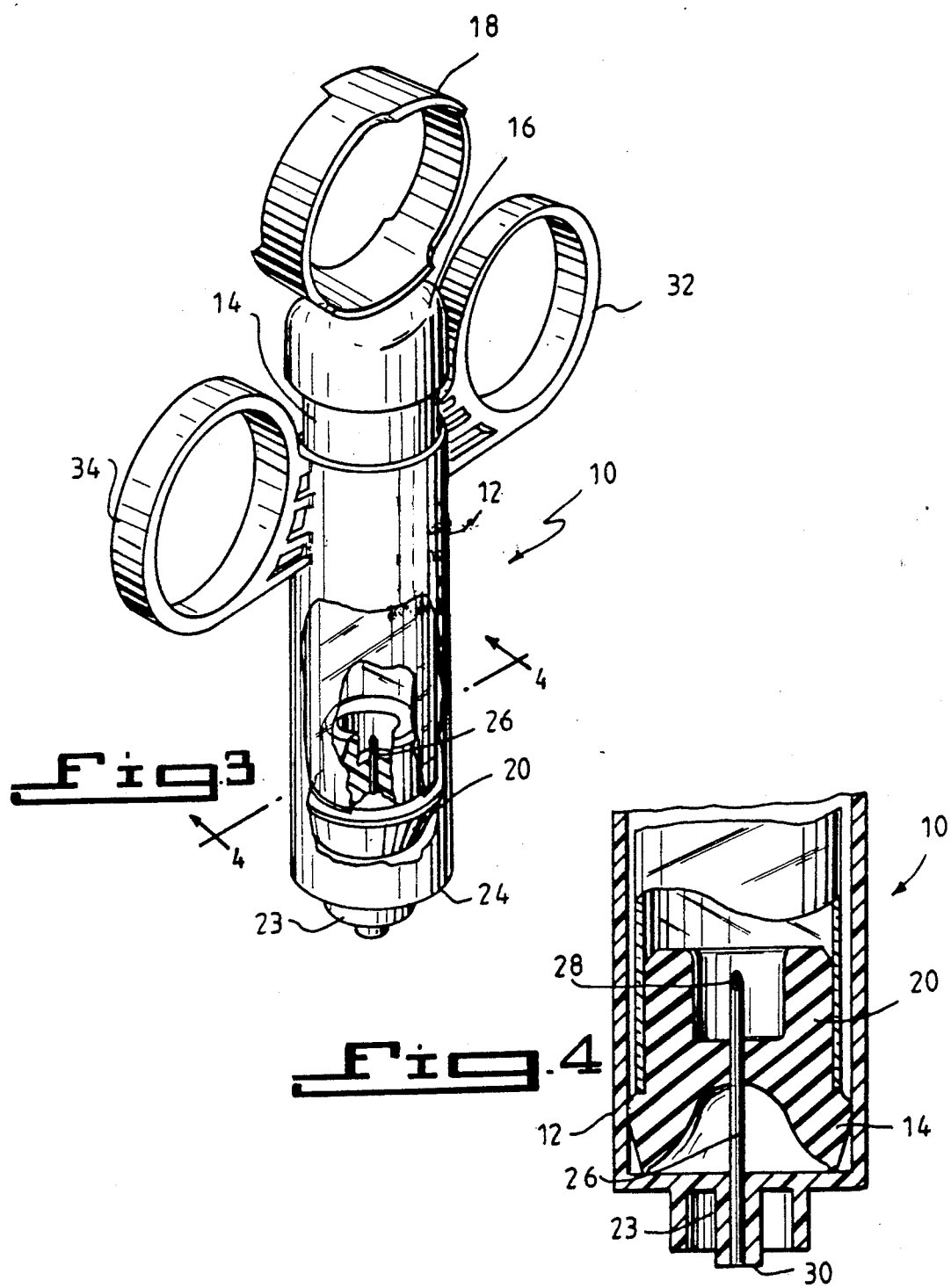

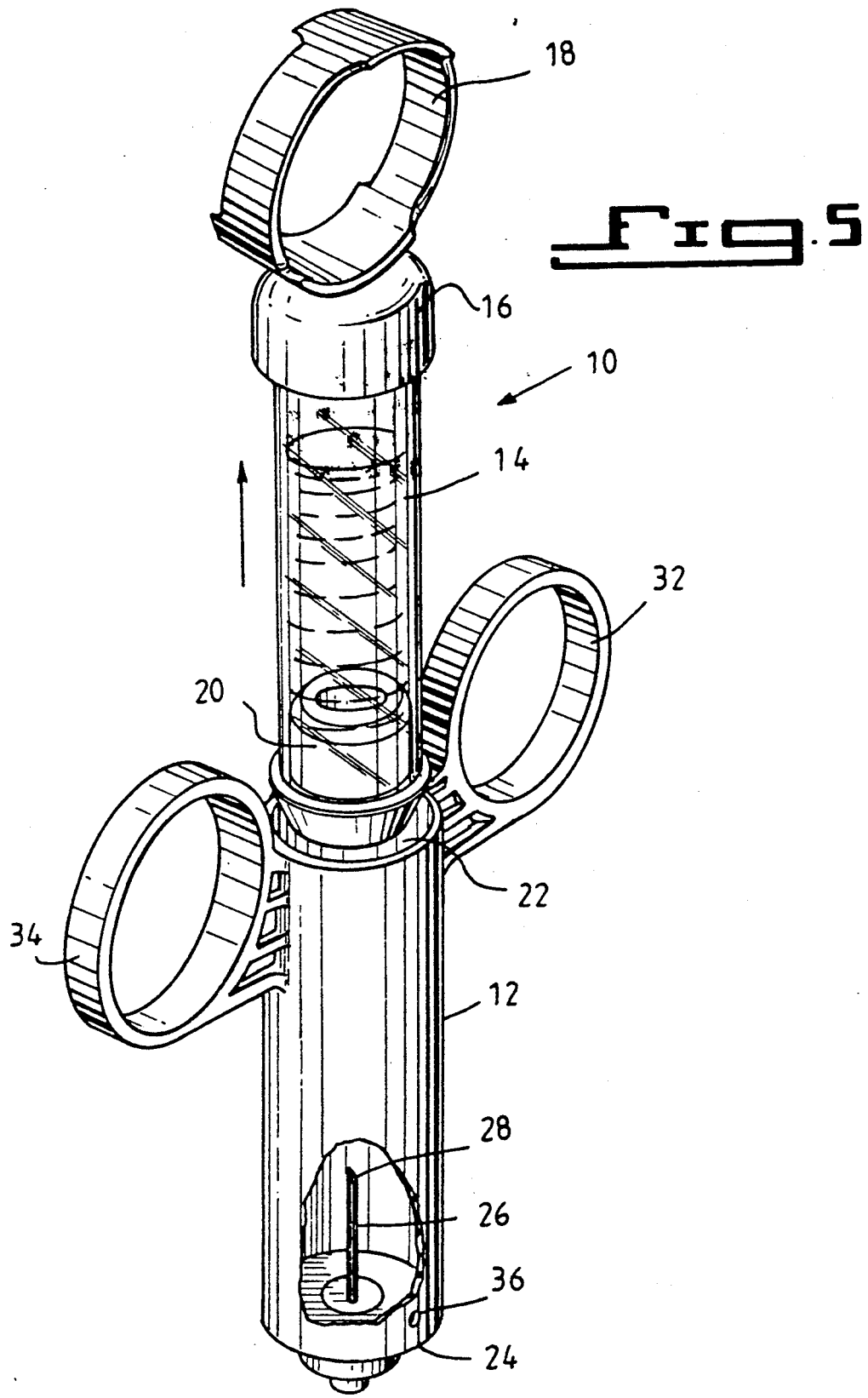

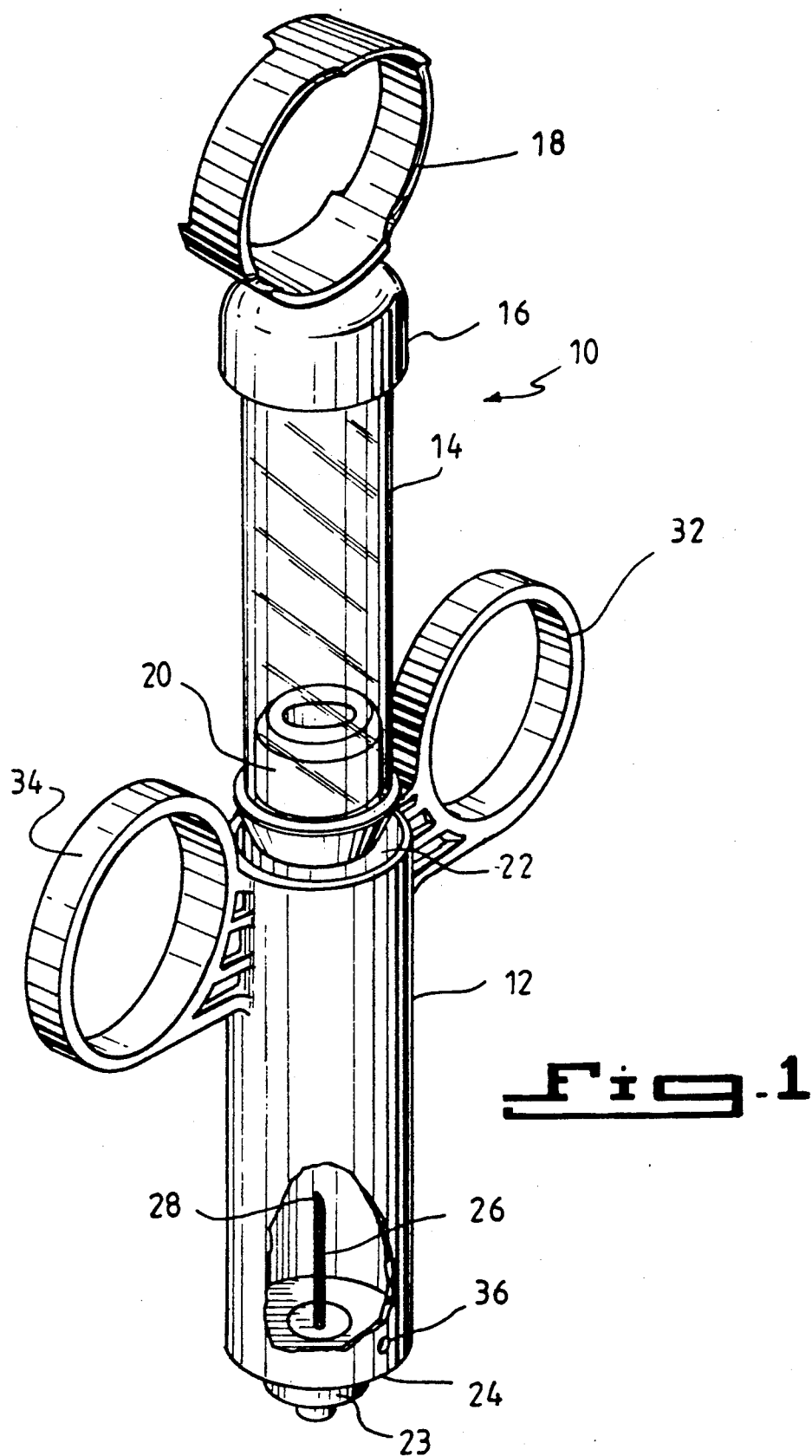

VACUUM BIOPSY APPARATUS

BACKGROUND OF THE INVENTION

The present invention relates to an apparatus usable for needle aspiration biopsy.

The use of suction or vacuum in conjunction with a fine-needle to collect biopsy specimens is known in the art. The use of a vacuum test tube in such a collection system is discussed in an article by Bruno D. Fornage, M.D. entitled "Fine-Needle Aspiration Biopsy with a Vacuum Test Tube" *Radiology* 1988:169:553:554.

Studies have demonstrated that the quality of the specimens obtained using a needle biopsy may be affected by the amount of and consistency of the suction or vacuum. Studies have also demonstrated that a significant portion of the specimen collected during needle biopsy is retained in the needle lumen. Thus it is useful to separate a collected specimen into two segments for further study: a first segment being the portion of the specimen in the needle lumen and a second segment being the portion of the specimen in the collection tube or syringe.

Due to the increase in infectious diseases such as AIDS and hepatitis, it has become increasingly important to minimize inadvertent contamination of medical personnel performing needle biopsies and other procedures. In known systems used for needle aspiration biopsy the collected specimen must be transferred from the collection device to slides and test tubes for further studies. During this transfer medical personnel may become contaminated by the specimen. Additionally the collected specimen may become contaminated or otherwise damaged during the transference process. This is particularly a problem if, as heretofore described, the specimen is separated into two segments. To do this the collecting person must separate the needle from the syringe and transfer both the specimen in the needle and in the syringe to other containers.

The use of sealed vacuum tubes connected to a needle is known for the collection of blood. The use of these sealed vacuum tubes minimizes contamination of the technician taking the blood and of the blood itself. Although these known systems are useful for blood collection, their design does not lend itself to use in needle biopsy since these devices do not provide as mechanism for safely separating the collected specimen into two portions.

Accordingly it is an object of the invention to provide a device for needle biopsy which permits the safe collection of the biopsy specimen and the safe segregation of that portion of the specimen in the needle lumen from the remainder of the specimen.

BRIEF DESCRIPTION OF INVENTION

In brief the present invention relates to a vacuum biopsy apparatus for use in the safe collection of biopsy specimens. The apparatus includes a syringe bearing an inwardly directed needle at one end thereof and having an open second end. The apparatus further includes a vacuum tube which carries a septum on one end thereof. The vacuum tube is shaped and dimensioned to fit within the syringe. The septum of the vacuum tube is shaped and dimensioned to fit within the syringe with a fluid-tight fit. The vacuum tube due to its dimensions can act as a plunger within the syringe. The syringe is formed with a small hole on its sidewall which prevents any accidental expulsion of air from the syringe's Luer Taper while the plunger is moved in a forward direction therein.

DESCRIPTION OF THE DRAWINGS

FIG. 1 is a perspective view of the vacuum biopsy device of the present invention showing the vacuum tube before it is inserted into the syringe.

FIG. 2 is a partially broken away perspective view of the FIG. 1 device showing the vacuum tube partially inserted into the syringe.

FIG. 3 is a view analogous to FIG. 2 showing the vacuum tube fully inserted into the syringe.

FIG. 4 is a sectional view taken along line 4—4 of FIG. 3.

FIG. 5 is a analogous to FIG. 2 showing the vacuum tube after a specimen is collected and the tube has been withdrawn from the syringe.

DETAILED DESCRIPTION OF THE PREFERRED EMBODIMENT

Referring now to the drawings the reference numeral 10 generally denotes the vacuum biopsy apparatus of the present invention. Apparatus 10 includes a syringe portion 12 and an associated vacuum tube 14. Removably connected to vacuum tube 14, at one end thereof, is a cap 16 with a single finger ring 18.

As best shown in FIG. 2, vacuum tube 14 is shaped and dimensioned to fit within syringe 12, for movement there-within. Vacuum tube 14 carries, at another end, a septum 20. Septum 20 is received within syringe 12 with a fluid-tight fit which may be either a friction or interference fit. Because septum 20 fits so snugly into syringe 12 it is necessary to use a lubricant, such as silicone on the septum 20 prior to inserting the vacuum tube 14 in the syringe 12.

Syringe 12 is formed with first open end 22 to receive vacuum tube 14 and a second end 24 which includes a standard luer lock 23 which carries an inwardly extending needle 26. Syringe 12 is wider at its open end 22 then at its second end 24. Needle 26, at its inner end 28, is designed to puncture septum 20. At its outer end 30, needle 26 is designed to mate with an aspiration biopsy needle (not shown). This mating is easily achieved due to the use of standard luer lock 23. (See American National Standards Institute/Health Industry Manufacturer's Association MD 70.1-1983).

Syringe 12 proximate, to its open end 22, is formed with two opposed finger rings 32, 34. As shown in FIG. 2 when the vacuum tube 14 is within syringe 12, finger ring 18, in conjunction with finger rings 32, 34 provide a comfortable three ring structure for the operator of apparatus 10 to use during a biopsy procedure.

A hole 36 is formed in the sidewall of syringe 12 proximal to second end 24. In a preferred embodiment of the hole 36 is between 0.050 to 0.075 inches (0.1 to 0.2 centimeters) in diameter and is approximately between 0.118 to 0.125 inches (0.3 to 0.318 centimeters) from second end 24.

In use apparatus 10 works in the following manner. When it is desired to draw a biopsy specimen a biopsy needle is connected to inwardly extending needle 26, using luer lock 23. Vacuum tube 14 is then placed in syringe 12. Due to the fit of the vacuum tube 14 and the septum 20 within the syringe 12, hole 36 is needed to prevent any inspiration of air into a body as the vacuum tube moves within the syringe. As the vacuum tube advances within the syringe 12, septum 20 is punctured by inwardly extending needle 24 thereby placing the interior of the vacuum tube in communication with the biopsy needle 38. As this occurs the specimen is drawn into the vacuum tube 14 due to the pressure differential between the vacuum tube 14 and that portion of the body where the specimen is being withdrawn from. In a preferred embodiment of this invention the vacuum aspiration is done using 10 milliliters of vacuum, although other amounts of vacuum may be used.

After the specimen is drawn into the vacuum tube 14, apparatus 10 with the biopsy needle connected thereto is removed from the area being biopsied. Due to the fit of the vacuum tube 14 and its septum 20 in syringe 12 the vacuum tube can now serve as a syringe plunger to permit the safe and easy separation of the collected specimen into two groups. Vacuum tube 12 is drawn outwardly from syringe 12 a sufficient distance. The operator then covers hole 36 and advances the vacuum tube into the syringe. As this occurs that portion of the specimen held in the lumen of the biopsy needle will be expelled into an appropriate receptacle. Vacuum tube 14 is then withdrawn completely from the syringe 12. And, without the need for any addition transfer that portion of the specimen in the vacuum tube 14 can be further studied. Finger ring 18 is removable from the vacuum tube and thus the vacuum tube can be used in a standard centrifuge. Until finger ring 18 is removed it can provide a convenient means for holding the vacuum tube. At this point, syringe 12 with the biopsy needle attached thereto can be safely disposed of.

In the preferred embodiment of the present invention syringe 12, and cap 16 are made of injection molded polypropylene. They can be made of other appropriate semi-translucent materials. The syringe 12 is about 3.16 inches (8.026 centimeters) long and has an upper inner diameter of about 0.690 inches (1.753 centimeters) and a lower diameter of about 0.656 inches (1.66 centimeters). Vacuum tube 14 is about 3.93 inches (9.98 centimeters) long and has an outer diameter of about 0.60 inches (1.52 centimeters). The portion of septum 20 which first enters the syringe 12 has an outer diameter of about 0.690 inches (1.753 centimeters). Septum 20 is made of rubber which is slightly compressible. Inner needle 24 is about 1.01 inches long. Rings 18, 40, 42 are each formed of polypropylene and have inner diameters of 1.00 inches.

In keeping with the purpose of this invention apparatus 10 provides a safe and convenient means for taking a biopsy specimen. Although its use has been described for this purpose the apparatus can also be used to safely take specimens of body fluids and tissues for other purposes.

What is claimed:
1. A vacuum biopsy apparatus comprising:
a syringe having a sidewall defining a chamber;
a vacuum tube receivable within said syringe chamber and carrying a septum at one end thereof, said septum being shaped and dimensioned to be received within said syringe chamber with a fluid-tight fit, said vacuum tube and septum together capable of movement within said syringe chamber to thus enable said vacuum tube to serve as a syringe plunger;
an inwardly projecting needle having two ends, one needle end adapted for connection to a biopsy needle and the other needle end capable of piercing said vacuum tube septum, said inwardly projecting needle when connected to a biopsy needle permitting said vacuum tube to communicate with said biopsy needle when said vacuum tube in within said syringe; and
venting means on said syringe sidewall to prevent expelling air from said syringe into the needle when said vacuum tube is moved within said syringe chamber said venting means being positioned below said other needle end and being accessible to the hand of a user.

2. The biopsy apparatus of claim 1 wherein said syringe has an upper larger diameter segment and a lower smaller diameter segment.

3. The biopsy apparatus of claim 1 wherein said syringe is semi-translucent.

4. The biopsy apparatus of claim 1 wherein said venting means is a hole formed in the syringe sidewall.

5. The biopsy apparatus of claim 4 wherein said hole has a diameter of between about 0.050 inches to 0.075 inches.

6. The biopsy apparatus of claim 5 wherein said hole is positioned between about 0.118 and 0.125 inches from the end of the syringe which carries the mating means.

7. The biopsy apparatus of claim 1 wherein said syringe has a first inner diameter of about 0.690 inches and a second inner diameter of about 0.656 inches, said vacuum tube has an outer diameter of about 0.600 inches, and at least a portion of said septum has an outer diameter of about 0.690 inches.

8. The biopsy apparatus of claim 7 wherein said septum is made of rubber.

9. The biopsy apparatus of claim 1 wherein said septum is made of rubber.

10. The biopsy apparatus of claim 1 and further comprising a first finger ring associated with said vacuum tube and a second and third finger ring associate with said syringe, said finger rings together providing a means for easily using said apparatus.

11. The apparatus of claim 10 wherein said syringe and said finger rings are formed of polypropylene.

12. The apparatus of claim 1 wherein said syringe is formed of polypropylene.

13. The apparatus of claim 1 and further including a luer lock connected to said inwardly projecting needle.

14. A method for performing a needle aspiration biopsy comprising steps of:
placing a biopsy needle in a specimen to be collected;
providing a syringe having a sidewall defining a chamber, a venting means, and at one end of said syringe a luer lock carrying an inwardly projecting needle;
providing a vacuum tube having a septum at one end, said septum shaped and dimensioned to be received within said syringe chamber with a fluid tight fit;
connecting said luer lock to said biopsy needle;
inserting the vacuum tube into the syringe chamber such that the inwardly directed needle of the syringe pierces the vacuum tube septum, thus placing the biopsy needle in communication with the interior of the vacuum tube and causing specimen to be aspirated into the vacuum tube;
partially withdrawing the vacuum tube from the syringe chamber;
covering the syringe venting means;
then moving the vacuum tube forward in the syringe chamber so that any specimen in the biopsy needle lumen will be expelled therefrom;
fully withdrawing the vacuum tube from the syringe so that the material therewithin can be studied.

* * * * *